(12) United States Patent
Benedini et al.

(10) Patent No.: US 7,799,784 B2
(45) Date of Patent: Sep. 21, 2010

(54) QUINOXALINE DERIVATIVES OF ALPHA-2 ADRENERGIC AGONISTS

(75) Inventors: Francesca Benedini, Milan (IT); Francesco Impagnatiello, Milan (IT); Stefano Biondi, Milan (IT); Ennio Ongini, Milan (IT); Wesley Kwan Mung Chong, Encinitas, CA (US)

(73) Assignee: Nicox S.A., Sophia Antipolis-Valbonne (FR)

( * ) Notice: Subject to any disclaimer, the term of this patent is extended or adjusted under 35 U.S.C. 154(b) by 0 days.

(21) Appl. No.: 12/162,529

(22) PCT Filed: Feb. 2, 2007

(86) PCT No.: PCT/EP2007/051017

§ 371 (c)(1),
(2), (4) Date: Jul. 29, 2008

(87) PCT Pub. No.: WO2007/090793

PCT Pub. Date: Aug. 16, 2007

(65) Prior Publication Data

US 2008/0318965 A1    Dec. 25, 2008

(51) Int. Cl.
*A61K 31/495* (2006.01)
(52) U.S. Cl. .................. 514/249; 544/353; 548/348.1
(58) Field of Classification Search ........... 514/249; 544/353; 548/348.1
See application file for complete search history.

(56) References Cited

U.S. PATENT DOCUMENTS 4,517,199 A    5/1985    York, Jr.

FOREIGN PATENT DOCUMENTS

| WO | WO 2005/053685 A1 | 5/1985 |
| WO | WO 97/01339 A1 | 1/1997 |
| WO | WO 2005/054218 A1 | 6/2005 |

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner*—James O Wilson
*Assistant Examiner*—Douglas M Willis
(74) *Attorney, Agent, or Firm*—Arent Fox LLP

(57) ABSTRACT

The present invention relates to alpha2-adrenergic receptor agonist nitrooxyderivatives, including the following structure,

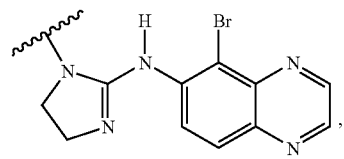

having improved pharmacological activity and enhanced tolerability. They can be employed for the treatment of ocular diseases, in particular high intraocular pressure and glaucoma.

6 Claims, No Drawings

QUINOXALINE DERIVATIVES OF ALPHA-2 ADRENERGIC AGONISTS

CROSS-REFERENCE TO RELATED APPLICATION

This application is a National Stage entry of International Application No. PCT/EP2007/051017, filed Feb. 2, 2007, the entire specification, claims and drawings of which are incorporated herewith by reference.

BACKGROUND OF THE INVENTION

The present invention relates to alpa$_2$-adrenergic receptor agonist nitrooxyderivatives and to their use for the treatment of ocular diseases in particular for the treatment of high intraocular pressure and glaucoma.

Glaucoma occurs in about 2% of all population over the age of 40 and may be asymptomatic for years before progressing to rapid loss of vision.

Glaucoma is primarily classified as open-angle, closed-angle, or congenital, and further classified as primary and secondary. Glaucoma is treated with a variety of pharmacological and surgical approaches. In cases where glaucoma is associated with ocular hypertension, pharmacological treatment comprises adrenergic agonists (epinephrine, dipevefrin, apraclonidine), cholinergic agonists (pilocarpine), beta blockers (betaxolol, levobunolol, timolol), carbonic anhydrase inhibitors (acetazolamide, clorzilamide) or more recently, prostaglandin analogues (latanoprost, bimatoprost) and alpha adrenergic agonists (brimonidine, apraclonidine). These pharmacological approaches help to restore the IOP to a normotensive state either by inhibiting the production of aqueous humor by the ciliary body, or facilitating aqueous humor outflow across the trabecular meshwork. In particular alpha-adrenergic agonists, such as brimonidine and apraclonidine, control IOP by reducing the production of aqueous humor as well as enhancing uveoscleral outflow.

Alpha$_2$-adrenergic receptor agonists are also used for the treatment of ocular hypertension and optic neuropathies both in monotherapy and as adjunctive therapy to beta-blockers. They are also used for the prophylactic treatment of acute pressure rises (i.e. before and after argon laser trabeculoplasty, cataract surgery, vitrectomy, peripheral iridotomy, capsulotomy). Their activity is due mainly to the activation of alpha$_2$-adrenergic receptors in the eye; such activation leads to reduction of acqueous humor production and increase in uveoscleral outflow. (Curr Opin Ophtalmol 1997, 8(2); 42-49)

It is known that optical ophthalmic solutions containing alpha$_2$-adrenergic receptor agonists are absorbed systemically and can produce side-effects including systemic hypotension, decreased heart rate, dry mouth, lid retraction, conjunctiva blanching, hyperaemia, burning, uveitis, tachyphilaxis, posterior segment vasoconstriction, topical allergy-like syndrome, increased pupil diameter, depression, anxiety, fatigue, nausea. (Hoyng and van Beek, Drugs, 59: 411-434 (2000), Surv Ophthalmol 1996, 41 Suppl 1: S19-26)

As described above, agents commonly used to treat glaucoma may cause adverse effects. Thus, there is a need for selective alpha$_2$-adrenergic receptor agonists that are both safe and effective in the treatment of ocular diseases and in particular glaucoma.

It has been surprisingly found that alpha$_2$-adrenergic receptor agonists nitrooxyderivatives of formula (I) have a significantly improved overall profile as compared to native compounds with respect to both pharmacological activity and enhanced tolerability.

BRIEF SUMMARY OF THE INVENTION

It is an object of the present invention alpha$_2$-adrenergic receptor agonists nitrooxyderivatives of general formula (I) and pharmaceutically acceptable salts or stereoisomers thereof:

wherein:

A is selected from

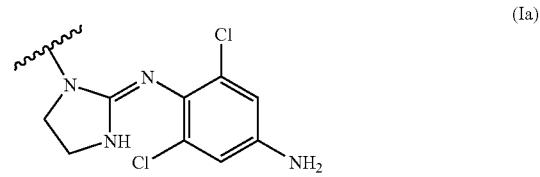

(Ia)

(Ib)

$X_1$ has the following meanings:
—C(O)—, —C(O)O—,

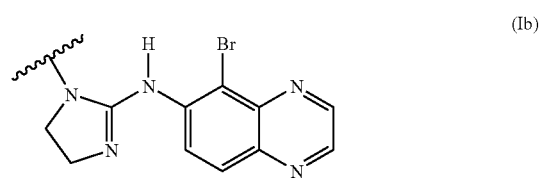

Y is a bivalent radical having the following meanings:

a)
straight or branched $C_1$-$C_{20}$ alkylene, preferably $C_1$-$C_{10}$, being optionally substituted with one or more of the substituents selected from the group consisting of: halogen atoms, hydroxy, —ONO$_2$ or $T_0$, wherein $T_0$ is —OC(O)($C_1$-$C_{10}$ alkyl)—ONO$_2$ or —O($C_1$-$C_{10}$ alkyl)—ONO$_2$;

cycloalkylene with 5 to 7 carbon atoms into cycloalkylene ring, the ring being optionally substituted with side chains T, wherein T is straight or branched alkyl with from 1 to 10 carbon atoms, preferably CH$_3$;

b)

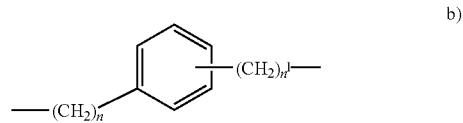

c)
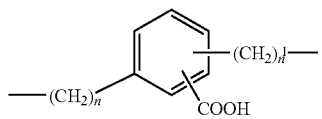

wherein n is an integer from 0 to 20, preferably n is from 1 to 10, $n^1$ is an integer from 1 to 20, preferably $n^1$ is from 1 to 10;

d)
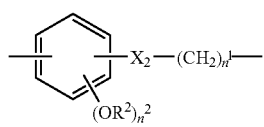

wherein:

$n^1$ is as defined above and $n^2$ is an integer from 0 to 2;
$X_2$=—OCO— or —COO— and $R^2$ is an hydrogen atom or $CH_3$;

e)
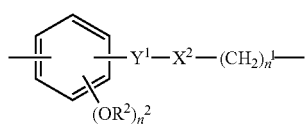

wherein:

$n^1$, $n^2$, $R^2$ and $X_2$ are as defined above;
$Y^1$ is —$CH_2$—$CH_2$— or —CH=CH—$(CH_2)_n{}^2$—;

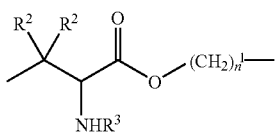

wherein:

$n^1$ and $R^2$ are as defined above, $R^3$ is H or —$COCH_3$;

with the proviso that when Y is selected from the bivalent radicals mentioned under b)-f), the —$ONO_2$ group is linked to a —$(CH_2)_n{}^1$ group;

g)
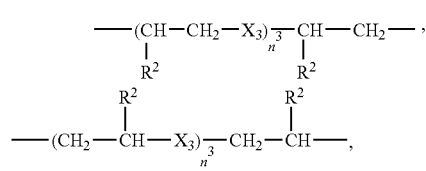

wherein $X_3$ is an oxygen atom or a sulphur atom, preferably $X_3$ is an oxygen atom;

n is an integer from 1 to 6, preferably from 1 to 4, $R^2$ is as defined above;

h)
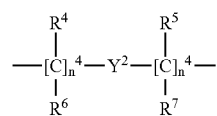

wherein:

$n^4$ is an integer from 0 to 10;

$n^5$ is an integer from 1 to 10;

$R^4$, $R^5$, $R^6$, $R^7$ are the same or different, and are H or straight or branched $C_1$-$C_4$ alkyl, preferably $R^4$, $R^5$, $R^6$, $R^7$ are H;

wherein the —$ONO_2$ group is linked to

wherein $n^5$ is as defined above;

$Y^2$ is an heterocyclic saturated, unsaturated or aromatic 5 or 6 members ring, containing one or more heteroatoms selected from nitrogen, oxygen, sulfur, and is selected from

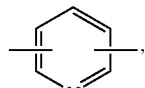 (Y1)

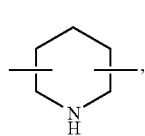 (Y2)

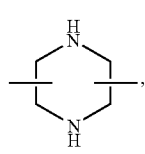 (Y3)

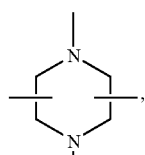 (Y4)

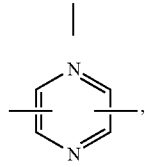 (Y5)

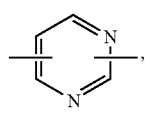 (Y6)

-continued

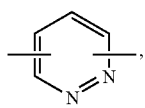 (Y7)

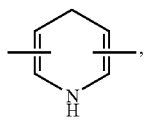 (Y8)

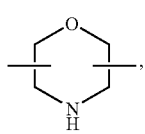 (Y9)

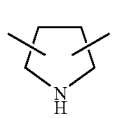 (Y10)

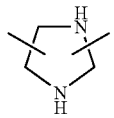 (Y11)

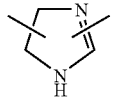 (Y12)

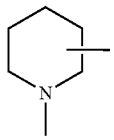 (Y13)

DETAILED DESCRIPTION OF THE INVENTION

The term "$C_1$-$C_{20}$ alkylene" as used herein refers to branched or straight chain $C_1$-$C_{20}$ hydrocarbon, preferably having from 1 to 10 carbon atoms such as methylene, ethylene, propylene, isopropylene, n-butylene, pentylene, n-hexylene and the like.

The term "$C_1$-$C_{10}$ alkyl" as used herein refers to branched or straight chain alkyl groups comprising one to ten carbon atoms, including methyl, ethyl, n-propyl, isopropyl, n-butyl, isobutyl, t-butyl, pentyl, hexyl, octyl and the like.

The term "cycloalkylene" as used herein refers to ring having from 5 to 7 carbon atoms including, but not limited to, cyclopentylene, cyclohexylene optionally substituted with side chains such as straight or branched ($C_1$-$C_{10}$)-alkyl, preferably $CH_3$.

The term "heterocyclic" as used herein refers to saturated, unsaturated or aromatic 5 or 6 members ring, containing one or more heteroatoms selected from nitrogen, oxygen, sulphur, such as for example pyridine, pyrazine, pyrimidine, pyrrolidine, morpholine, imidazole and the like.

Preferred nitrooxyderivatives of formula (I) are:

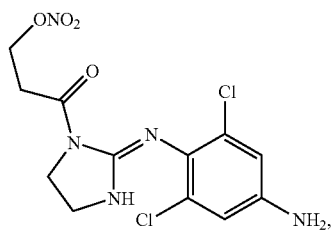 (1)

 (2)

 (3)

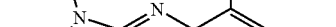 (4)

 (5)

 (6)

-continued
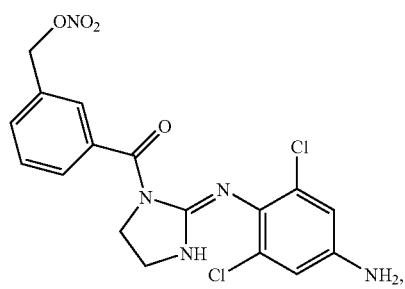
(7)
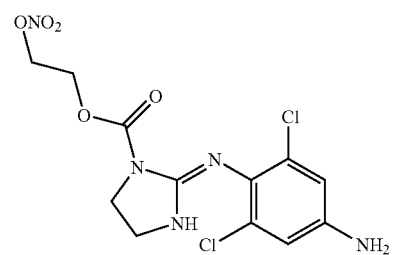
(12)
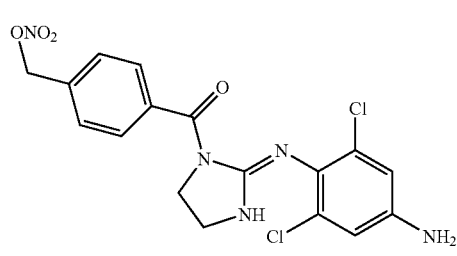
(8)
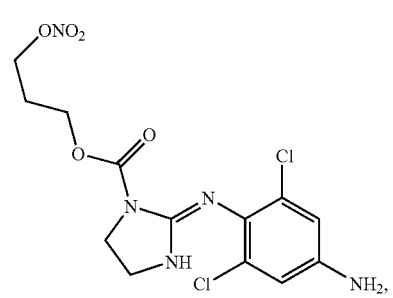
(13)
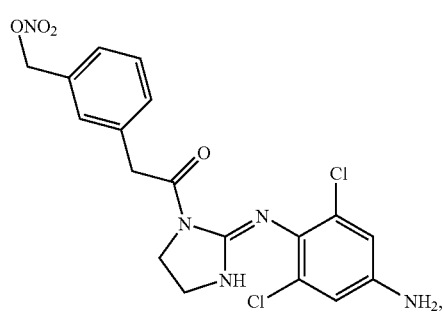
(9)
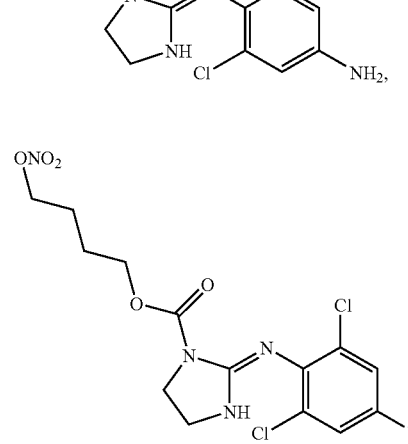
(14)
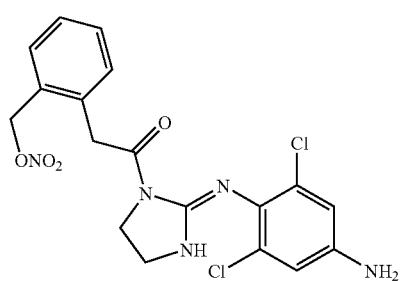
(10)
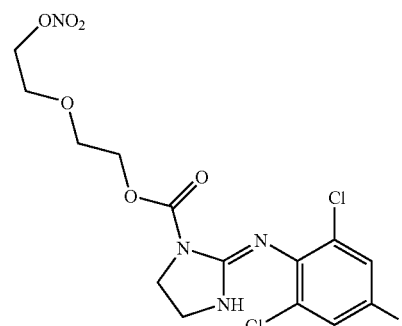
(15)
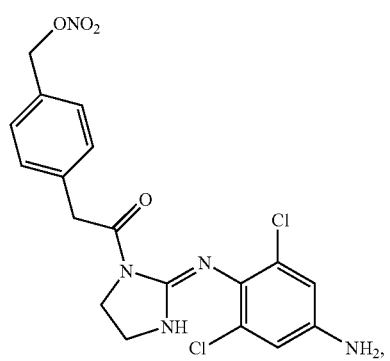
(11)
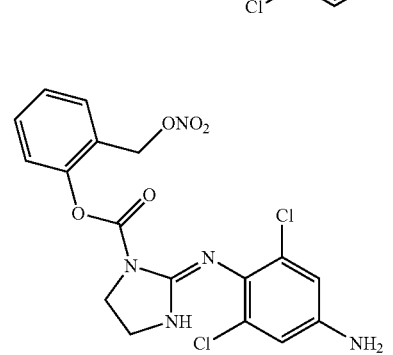
(16)

-continued
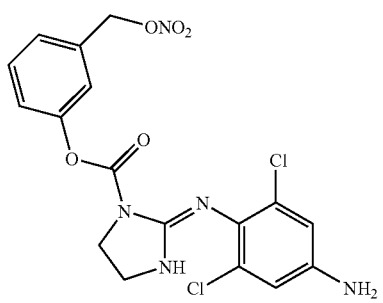
(17)
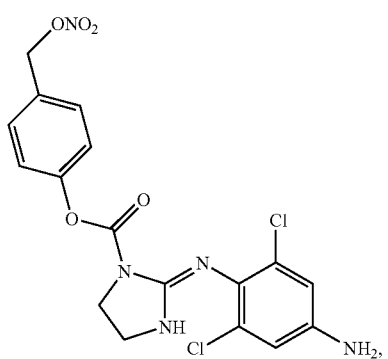
(18)
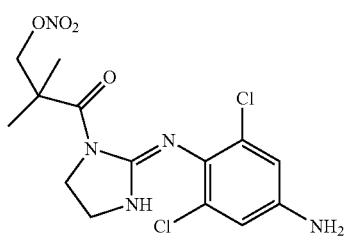
(19)
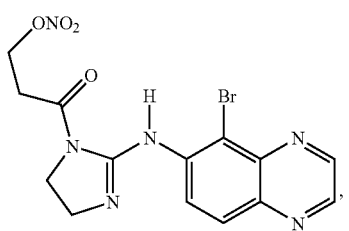
(20)
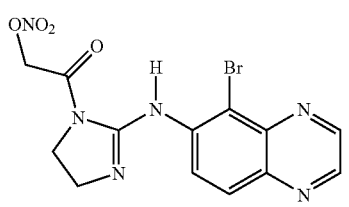
(21)
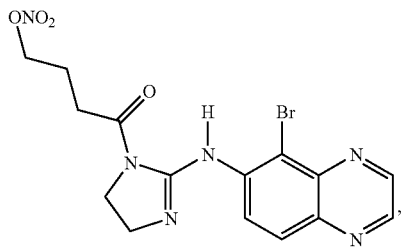
(22)
-continued
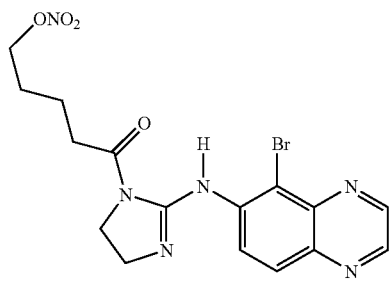
(23)
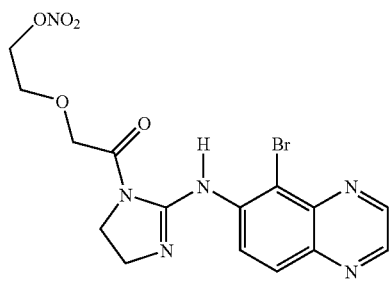
(24)
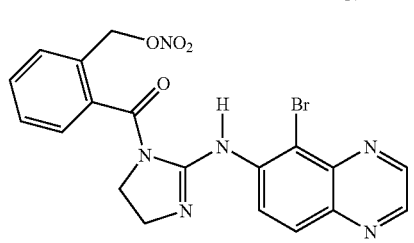
(25)
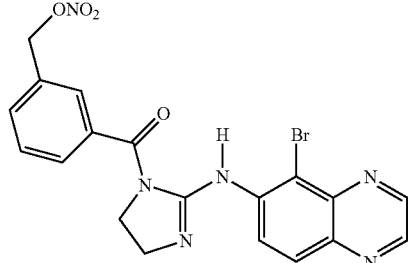
(26)
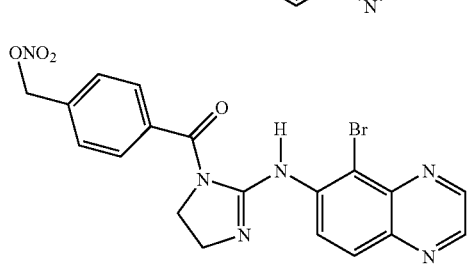
(27)
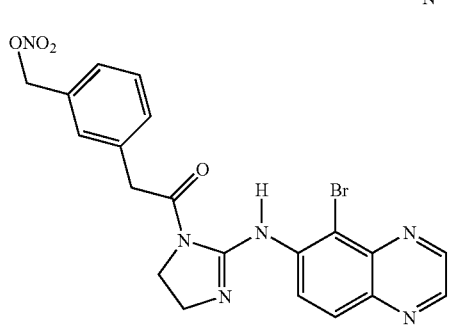
(28)

(29)
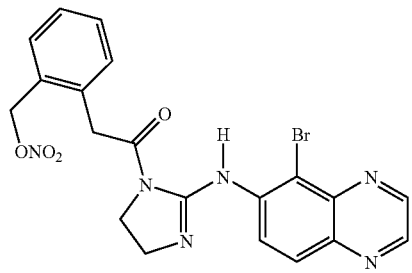
(30)
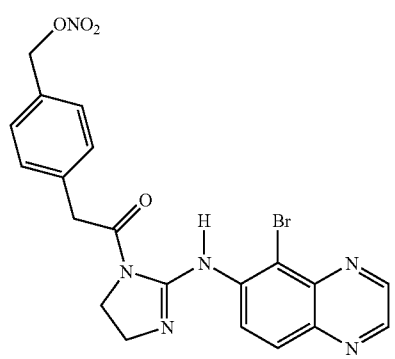
(31)
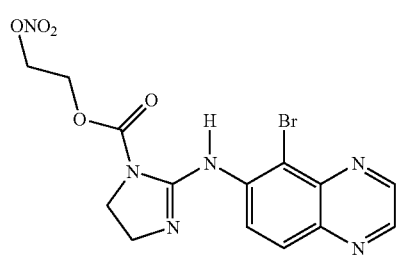
(32)
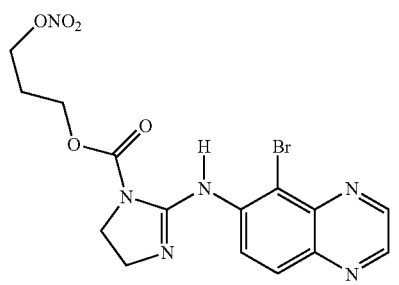
(33)
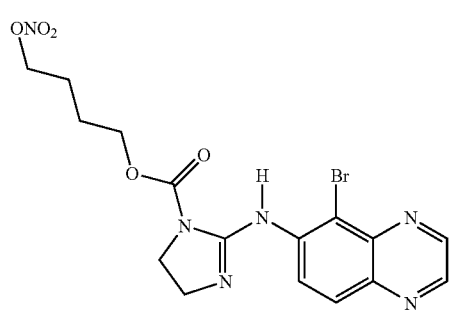
(34)
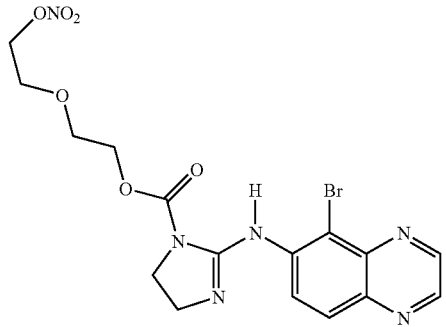
(35)
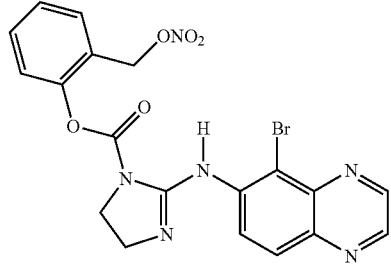
(36)
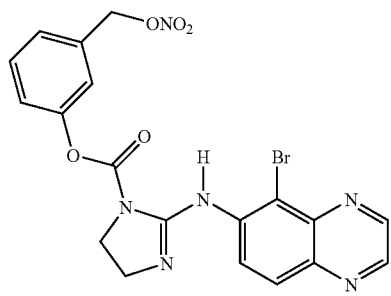
(37)
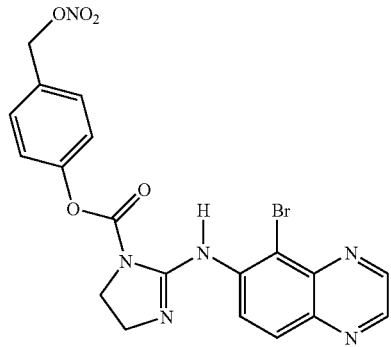
(38)
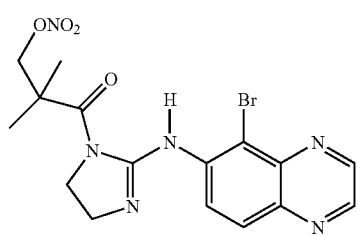

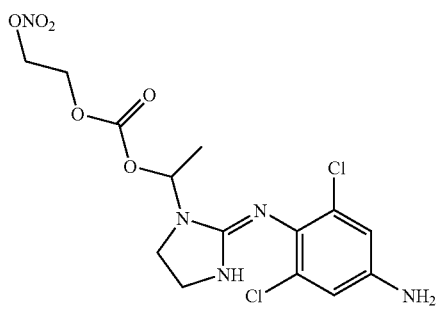
(39)
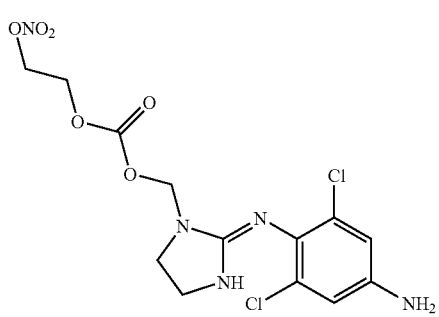
(40)
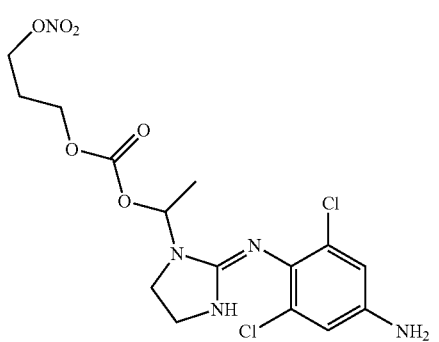
(41)
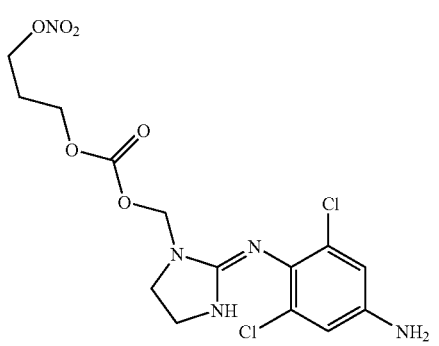
(42)
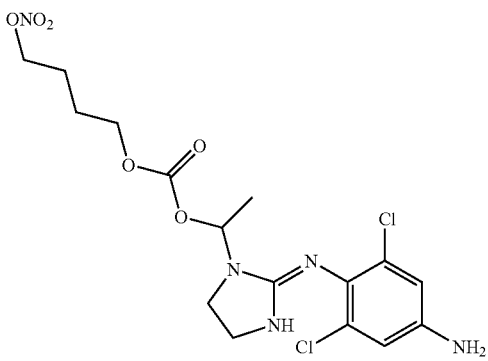
(43)
(44)
(45)
(46)

-continued
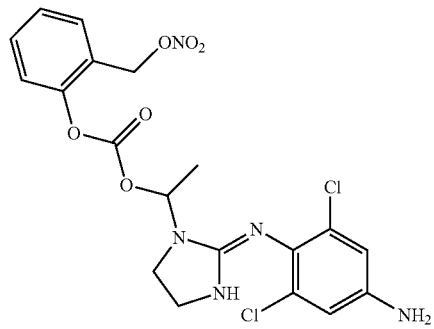
(47)
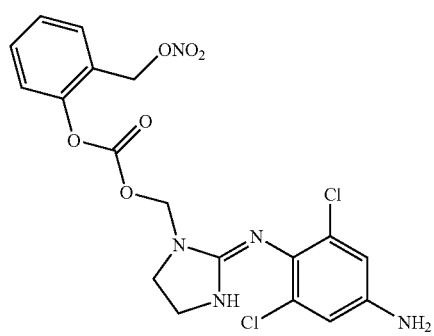
(48)
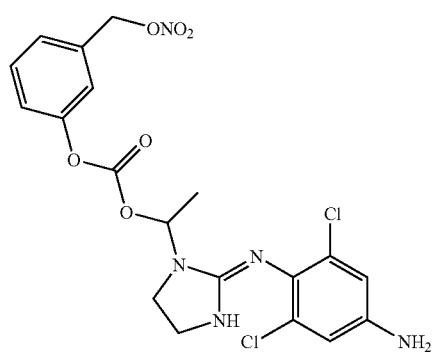
(49)
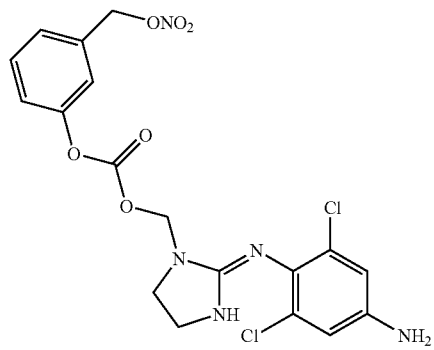
(50)
-continued
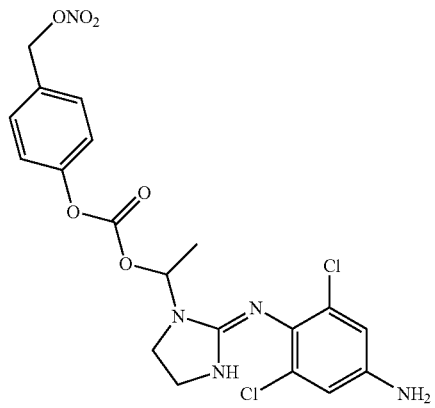
(51)
(52)
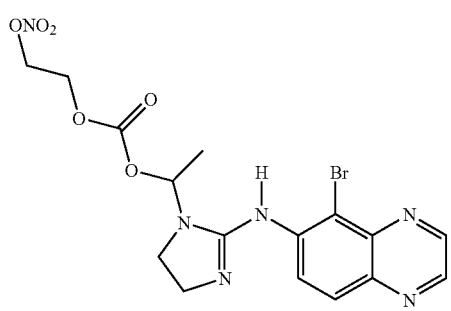
(53)
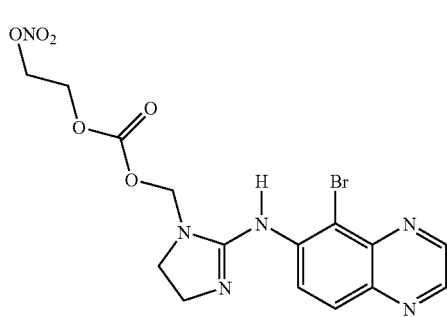
(54)

(55)
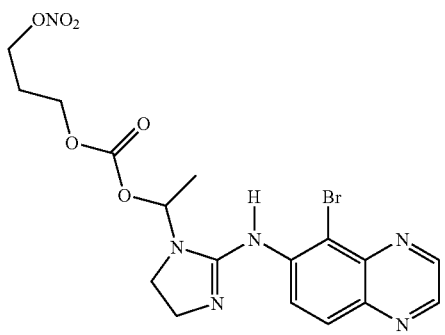
(59)
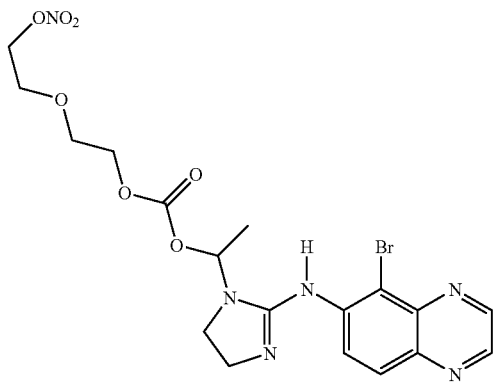
(56)
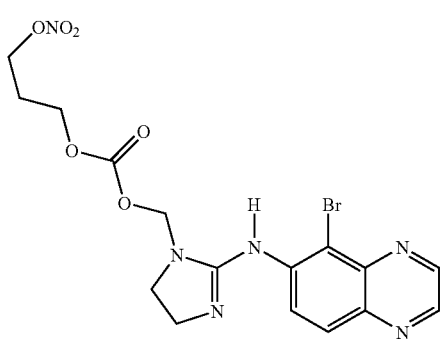
(60)
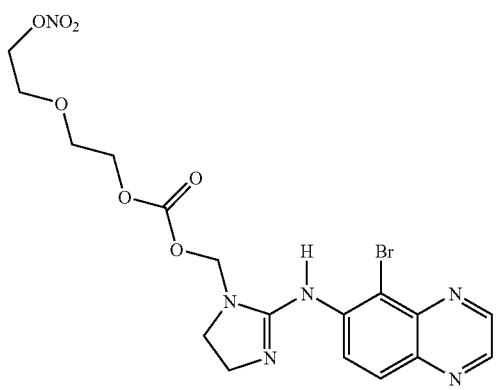
(57)
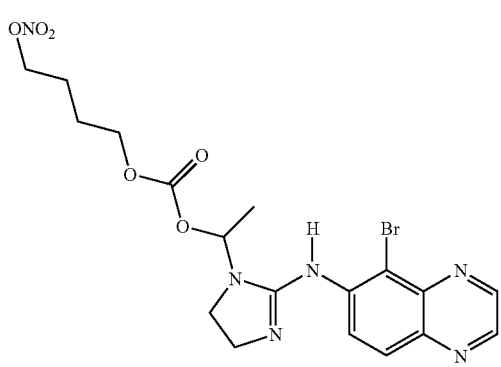
(61)
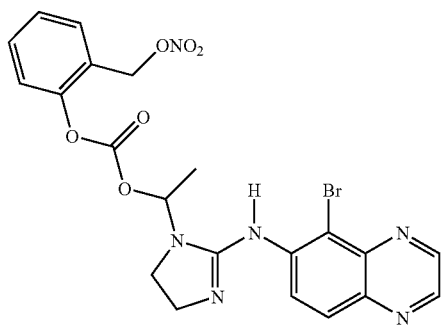
(58)
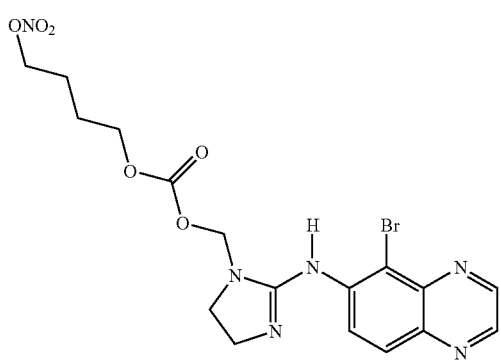
(62)
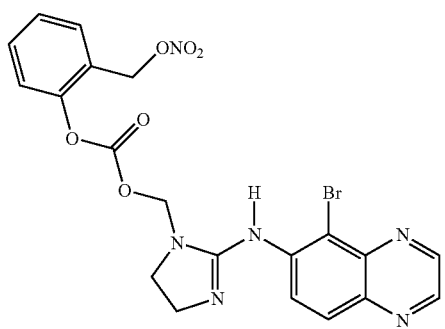

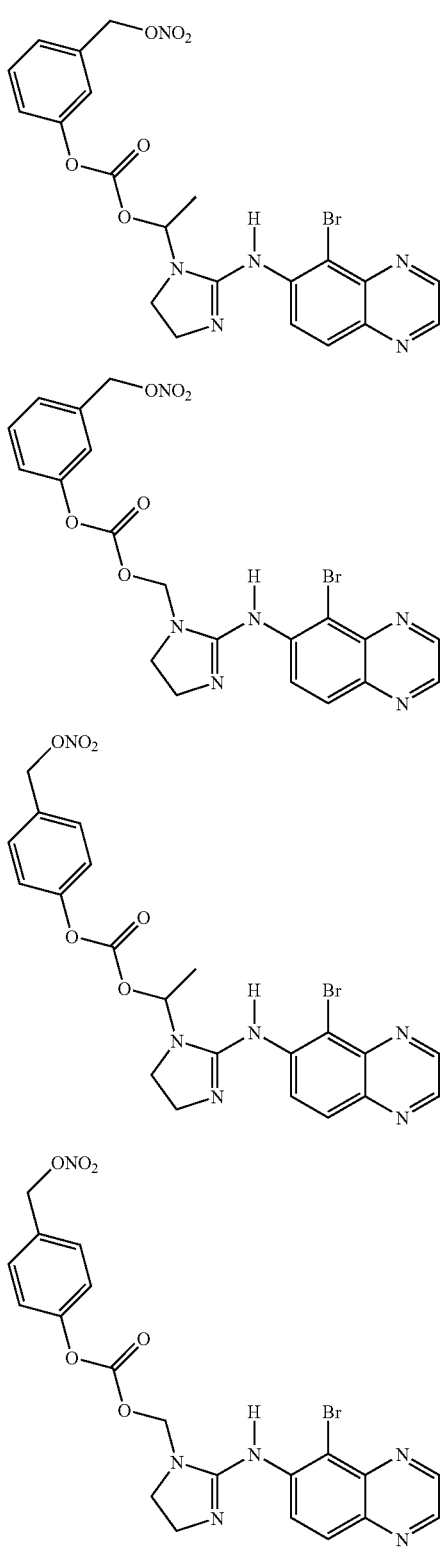

(63)

(64)

(65)

(66)

Another object of the present invention is pharmaceutical compositions containing at least a compound of the present invention of formula (I) together with non toxic adjuvants and/or carriers usually employed in the pharmaceutical field.

The preferred route of administration is topical.

The compounds of the present invention can be administered as solutions, suspensions or emulsions (dispersions) in an ophthalmically acceptable vehicle. The term "ophthalmically acceptable vehicle" as used herein refers to any substance or combination of substances which are non-reactive with the compounds and suitable for administration to patient.

Preferred are aqueous vehicles suitable for topical application to the patient's eyes.

Other ingredients which may be desirable to use in the ophthalmic compositions of the present invention include antimicrobials, preservatives, co-solvents, surfactants and viscosity building agents.

The invention also relates to a method for treating glaucoma or ocular hypertension, said method consisting in contacting an effective intraocular pressure reducing amount of a composition with the eye in order to reduce eye pressure and to maintain said pressure on a reduced level.

The doses of the compounds of the invention can be determined by standard clinical techniques and are in the same range or less than those described for the corresponding underivatized, commercially available compounds as reported in the: Physician's Desk Reference, Medical Economics Company, Inc., Oradell, N.J., 58$^{the}$ Ed., 2004; The pharmacological basis of therapeutics, Goodman and Gilman, J. G. Hardman, L. e. Limbird, Tenth Ed.

The treatment may be advantageously carried out in that one drop of the composition, corresponding to about 30 μl, is administered about several times per day, for example from 1 to 3 times, to the patient's eye.

It is further contemplated that the compounds of the present invention can be used with other medicaments known to be useful in the treatment of glaucoma or ocular hypertension, either separately or in combination. For example the compounds of the present invention can be combined with (i) beta-blockers, such as timolol, betaxolol, levobunolol and the like (see U.S. Pat. No. 4,952,581); (ii) carbonic anhydrase inhibitors, such as brinzolamide.

Also contemplated is the combination with nitrooxy derivatives of the above reported compounds, for example nitrooxy derivatives of beta-blockers such as those described in U.S. Pat. No. 6,242,432.

The compounds of the present invention can be synthesised as follows.

A) The compounds of general formula (I) wherein A is the radical (Ia) or (Ib), $X_1$ is —C(O)—, and Y is as above defined, can be obtained by a process comprising:

1A) reacting a compound of formula (IIIa) or (IIIb)

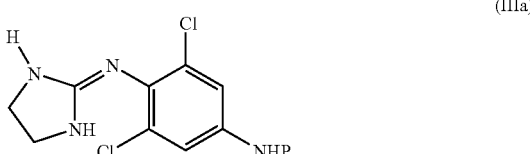

(IIIa)

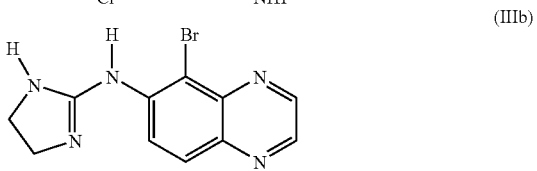

(IIIb)

wherein

P is H or a amino protecting group such as t-butoxycarbonyl and those described in T. W. Greene "Protective groups in organic synthesis", Harvard University Press, 1980; with a compound of formula (1a):

Act—C(O)—Y—ONO$_2$ (1a)

wherein Y are as above defined and wherein Act is a carboxylic acid activating group used in peptide chemistry such as:

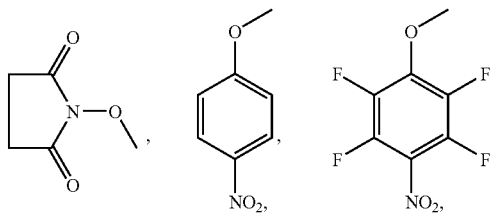

1A.a) removing the protective group of the compounds obtained in presence of a strong acid, such as HCl in dioxane or trifluoroacetic acid, as described in T. W. Greene "Protective groups in organic synthesis", Harvard University Press, 1980, and optionally converting the resulting compound of general formula (I) into a pharmaceutically acceptable salt thereof.

The reaction of a compound of formula (IIIa) or (IIIb), wherein P is as above defined, with a compound of formula (1a) wherein Y is as above defined and Act a carboxylic acid activating group used in peptide chemistry as above defined, may be carried out in presence of a inorganic or organic base in an aprotic polar/non-polar solvent such as DMF, THF, acetone or CH$_2$Cl$_2$ at temperatures range between 0°-65° C. or in a double phase system H$_2$O/Et$_2$O at temperatures range between 20°-40° C.; or in the presence of DMAP and a Lewis acid such as Sc(OTf)$_3$ or Bi(OTf)$_3$ in solvents such as DMF, CH$_2$Cl$_2$.

1A.b) The compound of formula (IIIa), wherein P is an hydrogen atom, which is known as apraclonidine is commercially available or can be synthesized as described in U.S. Pat. No. 4,517,199; the compound of formula IIIB, which is known as brimonidine, is commercially available or can be synthesised as according to the method described in U.S. Pat. No. 3,890,319.

1A.c) The compounds of formula (Ia) wherein Act is carboxylic acid activating group used in peptide chemistry as above defined, are obtained by reacting the acids (1b)

HOOC—Y—ONO$_2$ (1b)

wherein Y is as above defined, with the commercially available compounds (1c)

Act—H (1c)

wherein Act is as above defined, by conventional esterification reaction with condensing agents as DCC, EDAC.HCl as well known in the literature.

1A.d) The compounds of formula (Ib) as above defined are obtained by reacting the commercially available acids of formula (1d)

Hal—Y—COOH (1d)

with AgNO$_3$ in a suitable organic solvent such as acetonitrile or tetrahydrofurane (THF) under nitrogen in the dark at temperatures range between 20° to 80° C.; alternatively the reaction with AgNO$_3$ can be performed under microwave irradiation in solvents such acetonitrile or THF at temperatures in the range between 70-180° C. for short time (1-60 min).

2A) Alternatively, the compounds of general formula (I) wherein A is the radical (Ia) or (Ib), X$_1$ is —C(O)—, and Y is as above defined, can be obtained by a process comprising:

2A.a) reacting a compound of formula (IIIa) or (IIIb)

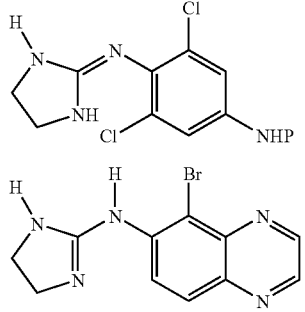

wherein

P is H or a amino protecting group such as t-butoxycarbonyl and those described in T. W. Greene "Protective groups in organic synthesis", Harvard University Press, 1980; with a compound of formula (1a'):

HO—C(O)—Y—ONO$_2$ (1a')

wherein Y is as above defined, and then removing the protective group of the compounds obtained as described in 1A.a); and optionally converting the resulting compounds of formula (I) into a pharmaceutically acceptable salt. The reaction of a compound of formula (IIIa) or (IIIb), wherein P is as above defined, with a compound of formula (1a') wherein Y is as above defined is carried out in presence of a condensing agent as dicyclohexylcarbodiimide (DCC), N'-(3-dimethylaminopropyl)-N-ethylcarbodiimide hydrochloride (EDAC) and a catalyst, such as N, N-dimethylamino pyridine (DMAP), or benzotriazol-1-yloxy-tris(dimethylamino) phosphonium hexafluorophosphate (BOP) and a organic base, such as N-methylmorpholine, N, N-diisopropylamine. The reaction is carried out in an inert organic solvent dry such as N, N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

2A.b) The compounds of formula (1a') as above defined are obtained by reacting the commercially available acids of formula (1d)

Hal—Y—COOH (1d)

with AgNO$_3$ in a suitable organic solvent such as acetonitrile or tetrahydrofurane (THF) under nitrogen in the dark at temperatures range between 20° to 80° C.; alternatively the reaction with AgNO$_3$ can be performed under microwave irradiation in solvents such acetonitrile or THF at temperatures in the range between 70-180° C. for short time (1-60 min).

2A.c) The compound of formula (IIIa), wherein P is an hydrogen atom, which is known as apraclonidine is commercially available or can be synthesized as described in U.S. Pat. No.

4,517,199; the compound of formula IIIB, which is known as brimonidine, is commercially available or can be synthesised as according to the method described in U.S. Pat. No. 3,890, 319.

3A) The compounds of general formula (I) wherein A is the radical (Ia) or (Ib), $X_1$ is —C(O)—, and Y is as above defined, can be obtained by a process comprising:

3A.a) reacting a compound of formula (IIIa) or (IIIb)

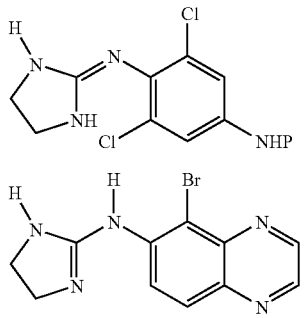

(IIIa)

(IIIb)

wherein

P is H or a amino protecting group such as t-butoxycarbonyl and those described in T. W. Greene "Protective groups in organic synthesis", Harvard University Press, 1980;

with a compound of formula (1a"):

Hal—C(O)—Y—ONO$_2$  (1a")

wherein Y are as above defined and wherein Hal is a chlorine atom or a bromine atom:

3A.b) removing the protective group of the compounds obtained as described in 1A.a), and optionally converting the resulting compound of general formula (I) into a pharmaceutically acceptable salt thereof. The reaction of a compound of formula (IIIa) or (IIIb), wherein P is as above defined, with a compound of formula (1a") wherein Y and Hal are as above defined, is carried out in presence of a inorganic or organic base in an aprotic polar/non-polar solvent such as DMF, THF, acetone or CH$_2$Cl$_2$ at temperatures range between 0°-65° C. or in a double phase system H$_2$O/Et$_2$O at temperatures range between 20°-40° C.; or in the presence of DMAP and a Lewis acid such as Sc(OTf)$_3$ or Bi(OTf)$_3$ in solvents such as DMF, CH$_2$Cl$_2$.

3A.c) The compound of formula (IIIa), wherein P is an hydrogen atom, which is known as apraclonidine, is commercially available or can be synthesized as described in U.S. Pat. No. 4,517,199; the compound of formula IIIB, which is known as brimonidine, is commercially available or can be synthesised as according to the method described in U.S. Pat. No. 3,890, 319.

3A.d) The compounds of formula (1a") wherein Hal is as above defined, are obtained by reacting the acids (1b)

HOOC—Y—ONO$_2$  (1b)

wherein Y is as above defined, with thionyl or oxalyl chloride, halides of P$^{III}$ or P$^V$ in solvents inert such as toluene, chloroform, DMF, at temperatures range between 20°-40° C.

3A.e) The compounds of formula (1b) as above defined are obtained by reacting the commercially available acids of formula (1d)

Hal—Y—COOH  (1d)

with AgNO$_3$ in a suitable organic solvent such as acetonitrile or tetrahydrofuran (THF) under nitrogen in the dark at temperatures range between 20° to 80° C.; alternatively the reaction with AgNO$_3$ can be performed under microwave irradiation in solvents such as acetonitrile or THF at temperatures in the range between 70-180° C. for short time (1-60 min).

B) The compounds of general formula (I) wherein A is the radical (Ia) or (Ib), $X_1$ is —C(O)O— and Y is as above defined, can be obtained by a process comprising:

1B) by reacting a compound of formula (IIIa) or (IIIb)

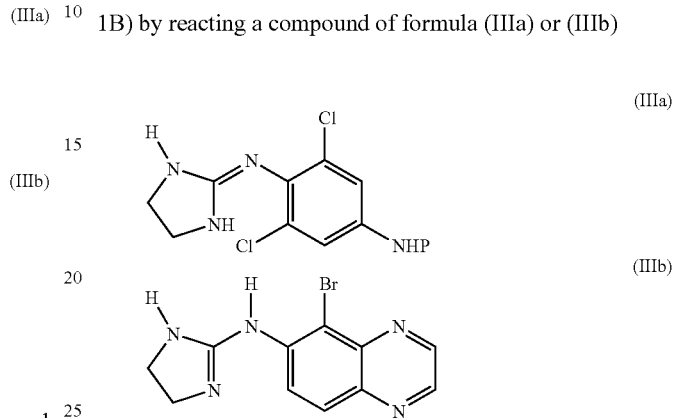

(IIIa)

(IIIb)

wherein

P is H or a amino protecting group such as t-butoxycarbonyl and those described in T. W. Greene "Protective groups in organic synthesis", Harvard University Press, 1980; with a compound of formula (1a.i)

Act—C(O)—O—Y—ONO$_2$  (1a.i)

wherein Act and Y are as above defined, in presence of a inorganic or organic base/DMAP in an aprotic polar/nonpolar solvent such as DMF, THF or CH$_2$Cl$_2$ at temperatures range between 0° to 65° C. or in a double phase system H$_2$O/Et$_2$O at temperatures range between 20° to 40° C.; or in the presence of DMAP and a Lewis acid such as Sc(OTf)$_3$ or Bi(OTf)$_3$ in solvents such as DMF, CH$_2$Cl$_2$;

and then removing the protective group of the compounds obtained as described in 1A.a); and optionally converting the resulting compounds of formula (I) into a pharmaceutically acceptable salt.

1B.a) The compounds of formula (1a.i) as above defined are obtained by reacting compounds of formula (1e)

Act—C(O)—Hal  (1e)

with a compounds of formula (1f)

HO—Y—ONO$_2$  (1f)

wherein Y is as above defined, in presence of an inorganic or organic base in an aprotic polar/non-polar solvent such as DMF, THF or CH$_2$Cl$_2$ at temperatures range between 0° to 65° C. or in a double phase system H$_2$O/Et$_2$O at temperatures range between 20° to 40° C., 1B.b) The compounds of formula (1f) are obtained by reacting the commercially available compounds of formula HO—Y—Hal (1f) wherein Y and Hal are as above defined, with AgNO$_3$ in a suitable organic solvent such as acetonitrile or tetrahydrofurane (THF) under nitrogen in the dark at temperatures range between 20°-80° C.; alternatively the reaction with AgNO$_3$ can be performed under microwave irradiation in solvents such acetonitrile or THF at temperatures in the range between about 100-180° C. for time range about 1-60 min.

The compounds of formula (1f) are commercially available or can be obtained by method well known in the literature;

1B.c) The compounds of formula (1e) as above defined are obtained by reacting compounds of formula (1c)

Act—H (1c)

wherein Act is as above defined, with phosgene and derivatives such as triphosgene, in the presence of a inorganic or organic base in an aprotic polar/non-polar solvent such as DMF, THF or CH$_2$Cl$_2$ at temperatures range between 0° to 65° C.

C) Alternatively, the compounds of general formula (I) wherein A is the radical (Ia) or (Ib), X$_1$ is —C(O)O— and Y is as above defined, can be obtained by a process comprising:

1C) reacting a compound of formula (IIIa) or (IIIb)

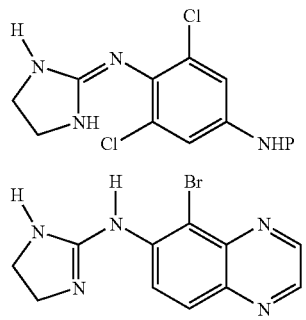

wherein

P is H or a amino protecting group such as t-butoxycarbonyl and those described in T. W. Greene "Protective groups in organic synthesis", Harvard University Press, 1980; with compounds of formula (1a.ii), Hal—C(O)—O—Y—ONO$_2$ (1a.ii)

wherein Hal is an halogen atom, preferably is Cl, and Y is as above defined, in presence of a inorganic or organic base/DMAP in an aprotic polar/non-polar solvent such as DMF, THF or CH$_2$Cl$_2$ at temperatures range between 0° to 65° C. or in a double phase system H$_2$O/Et$_2$O at temperatures range between 20° to 40° C.; or in the presence of DMAP and a Lewis acid such as Sc(Otf)$_3$ or Bi(OTf)$_3$ in solvents such as DMF, CH$_2$Cl$_2$; and then removing the protective group of the obtained compounds as described in 1A.a); and optionally converting the resulting compounds of formula (I) into a pharmaceutically acceptable salt.

1C.a) The compound of formula (IIIa), wherein P is an hydrogen atom, which is known as apraclonidine is commercially available or can be synthesized as described in U.S. Pat. No. 4,517,199; the compound of formula IIIB, which is known as brimonidine, is commercially available or can be synthesised as according to the method described in U.S. Pat. No. 3,890,319.

1C.b) The compounds of formula (1a.ii) as above defined, are obtained by reacting a compounds of formula (1f)

HO—Y—ONO$_2$ (1f)

and phosgene and its derivatives such as triphosgene in the presence of a inorganic or organic base in an aprotic polar/non-polar solvent such as DMF, THF or CH$_2$Cl$_2$ at temperatures range between 0° to 65° C., 1C.c) The compounds of formula (1f) are obtained as described in 1B.b).

D) The compounds of general formula (I) wherein A is the radical (Ia) or (Ib), X$_1$ is

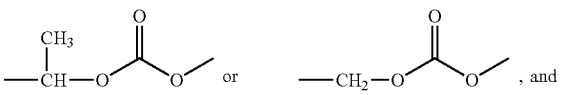

Y is as above defined, can be obtained by a process comprising:

1D) reacting a compound of formula (IIIa) or (IIIb)

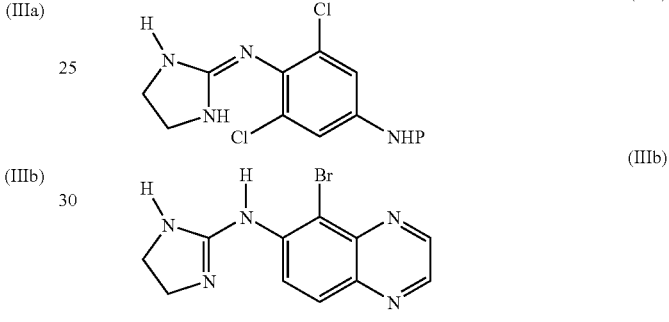

wherein

P is H or a amino protecting group such as t-butoxycarbonyl and those described in T. W. Greene "Protective groups in organic synthesis", Harvard University Press, 1980; with compounds of formula (1a.iii)

Hal—W$_4$—OC(O)O—Y—ONO$_2$ (1a.iii)

wherein Hal is an halogen atom and W$_4$ is —CH$_2$— or —CH(CH$_3$)—, in presence of a inorganic or organic base in an aprotic polar/non-polar solvent such as DMF, THF or CH$_2$Cl$_2$ at temperatures range between 0° to 65° C. or in a double phase system H$_2$O/Et$_2$O at temperatures range between 20° to 40° C.; and then removing the protective group of the obtained compounds as described in 1A.a).

1D.a) The compounds of formula (1a.iii) are obtained by reacting the commercially available haloalkylhalocarbonate of formula (1g)

Hal—W$_4$—OC(O)Hal (1g)

wherein Hal and W$_4$ are as above defined, with a compound of formula (1f)

HO—Y—ONO$_2$ (1f)

wherein Y is as above defined, in the presence of a inorganic or organic base in an aprotic polar or in an aprotic non-polar solvent such as DMF, THF or CH$_2$Cl$_2$ at temperatures range between 0° to 65° C., 1D.b) The compounds of formula (1f) are obtained as described in 1B.b).

E) The compounds of general formula (I) wherein A is the radical (Ia) or (Ib), $X_1$ is —C(O) or —C(O)O—, and Y is as above defined, can be obtained by a process comprising:

1E.a) reacting a compound of formula (IIIa') or (IIIb')

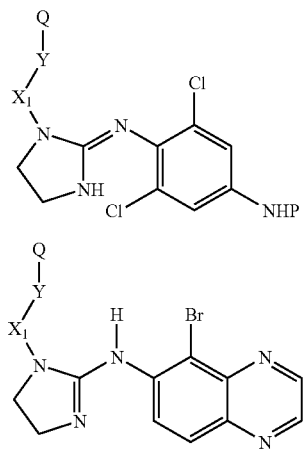

wherein Q is selected from a chlorine atom, a bromine atom, a iodine atom, mesyl, tosyl with a nitrate source such as silver nitrate, lithium nitrate, sodium nitrate, potassium nitrate, magnesium nitrate, calcium nitrate, iron nitrate, zinc nitrate or tetraalkylammonium nitrate (wherein alkyl is $C_1$-$C_{10}$ alkyl) in a suitable organic solvent such as acetonitrile, tetrahydrofurane, methyl ethyl ketone, ethyl acetate, DMF, the reaction is carried out, in the dark, at a temperature ranges from room temperature to the boiling point temperature of the solvent. The preferred nitrate source is silver nitrate; and then 1E.b) removing the protective group with the methods known in the art; and optionally converting the resulting compound of general formula (I) into a pharmaceutically acceptable salt.

1E.c) The compounds of formula (IIIa') or (IIIb') as above defined are obtained by reacting compounds of formula (IIIa) and (IIIb) wherein P is as above defined, with compounds of formula (1h)

Act—C(O)—Y—Hal (1h)

or compounds of formula (1l)

Act—C(O)—O—Y—Hal (1l)

wherein Hal is an halogen atom and Act, Y are as above defined, in presence of an inorganic or organic base/DMAP in an aprotic polar/non-polar solvent such as DMF, THF or $CH_2Cl_2$ at temperatures range between 0° to 65° C. or in a double phase system $H_2O/Et_2O$ at temperatures range between 20° to 40° C.; or in the presence of DMAP and a Lewis acid such as $Sc(OTf)_3$ or $Bi(OTf)_3$ in solvents such as DMF, $CH_2Cl_2$;

1E.d) The compounds of formula (1h)

Act—C(O)—Y—Hal (1h)

as above defined, are obtained by reacting commercially available (1c)

Act—H (1c)

with the commercially available compounds of formula (1d)

HO(O)C—Y—Hal (1d)

by conventional esterification reaction with condensing agents as DCC, EDAC.HCl as well known in the literature.

The compounds of formula (1l)

Act—C(O)—O—Y—Hal (1l)

as above defined, are obtained by reacting compounds of formula (1e)

Act—C(O)—Hal (1e)

which are commercially available or are obtained as described in 1B.c), with a compounds of formula (1f')

HO—Y—Hal (1f')

in presence of an inorganic or organic base in an aprotic polar/non-polar solvent such as DMF, THF or $CH_2Cl_2$ at temperatures range between 0° to 65° C. or in a double phase system $H_2O/Et_2O$ at temperatures range between 20° to 40° C.;

1E.e) The compound of formula (IIIa), wherein P is an hydrogen atom, which is known as apraclonidine is commercially available or can be synthesized as described in U.S. Pat. No. 4,517,199; the compound of formula IIIB, which is known as brimonidine, is commercially available or can be synthesised as according to the method described in U.S. Pat. No. 3,890,319.

F) Alternatively, the compounds of general formula (I) wherein A is the radical (Ia) or (Ib), $X_1$ is —C(O) or —C(O)O—, and Y is as above defined, can be obtained by a process comprising:

1F.a) reacting a compound of formula (IIIa") or (IIIb")

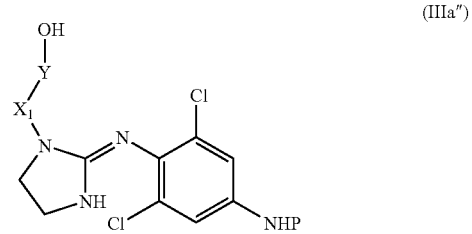

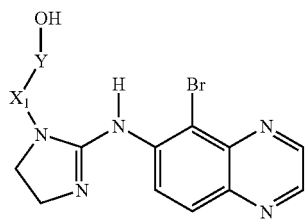

P is H or a amino protecting group such as t-butoxycarbonyl and those described in T. W. Greene "Protective groups in organic synthesis", Harvard University Press, 1980, with triflic anhydride/tetraalkylammonium nitrate salt in an aprotic polar/non-polar solvent such as DMF, THF or $CH_2Cl_2$ at temperatures range between −60° to 65° C.;

1F.b) removing the protective group with the methods known in the art; and optionally converting the compound of formula (I) into a pharmaceutically acceptable salt.

1F.c) The compounds of formula (IIIa") or (IIIb") are obtained by reacting the compounds of formula (IIIa) or (IIIb) wherein P is as above defined, with compounds of formula (1m)

Act—C(O)—Y—OH (1m)

or with compounds of formula (1n)

Act—C(O)—O—Y—OH (1n)

wherein Act and Y are as above defined, in presence of a inorganic or organic base/DMAP in an aprotic polar/non-polar solvent such as DMF, THF or $CH_2Cl_2$ at temperatures range between 0° to 65° C. or in a double phase system $H_2O/Et_2O$ at temperatures range between 20° to 40° C.; or in the presence of DMAP and a Lewis acid such as Sc $(OTf)_3$ or $Bi(OTf)_3$ in solvents such as DMF, $CH_2Cl_2$;

1F.d) The compounds of formula (1m)

Act—C(O)—Y—OH  (1m)

are obtained by reacting commercially available (1c)

Act—H  (1c)

with the commercially available compounds of formula (1o)

HOOC—Y—OH  (1o)

by conventional esterification reaction with condensing agents as DCC, EDAC.HCl as well known in the literature;

The compounds of formula (1n)

Act—C(O)—O—Y—OH  (1n)

are obtained by reacting compounds of formula (1e)

Act—C(O)—Hal  (1e)

which are commercially available or are obtained as described in 1B.c), with a compounds of formula (1j)

HO—Y—OH  (1j)

in presence of an inorganic or organic base in an aprotic polar/non-polar solvent such as DMF, THF or $CH_2Cl_2$ at temperatures range between 0° to 65° C. or in a double phase system $H_2O/Et_2O$ at temperatures range between 20° to 40° C.

Reagents and conditions: a) $AgNO_3$, $CH_3CN$, r.t., 24 h; b) Triphosgene, $Et_3N$, benzene, 0-20° C., 12 h; c) $Et_3N$, DMF, 40 h.

Abbreviations:
DMF=N, N-dimethylformamide
DCM=methylene chloride
$Et_2O$=diethyl ether
$Et_3N$=triethylamine
TFA=trifluoroacetic acid

EXAMPLE 1

2-[5-Bromo-quinoxalin-6-ylimino]-imidazolidine-1-carboxylic Acid 2-nitrooxy-ethyl Ester

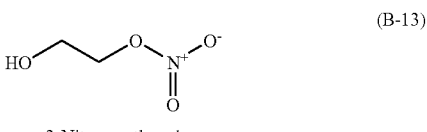

2-Nitroxy-ethanol

To a solution of 2-bromo-ethanol (2.5 g, 20 mmol) in dry $CH_3CN$ (5.0 mL) was added to a solution of $AgNO_3$ (4.08 g, 24 mmol) in dry $CH_3CN$ (20 mL) in dropwise. The solution was stirred for 24 h in darkness at room temperature. The reaction mixture was filtered and the collected solid was washed with $CH_3CN$. The filtrate was concentrated in vacuo and extracted with $CH_2Cl_2$. The organic layer was evaporated under vacuum to give Compound B-13 as a light yellow oil (1.07 g), with a similar NMR to that reported by Ziakas, G. N. et al, Bioorg. Med. Chem. 2005, 13, 6485-6492 and WO2004/031372. The crude product was used in the next step without further purification.

Scheme for Example 1

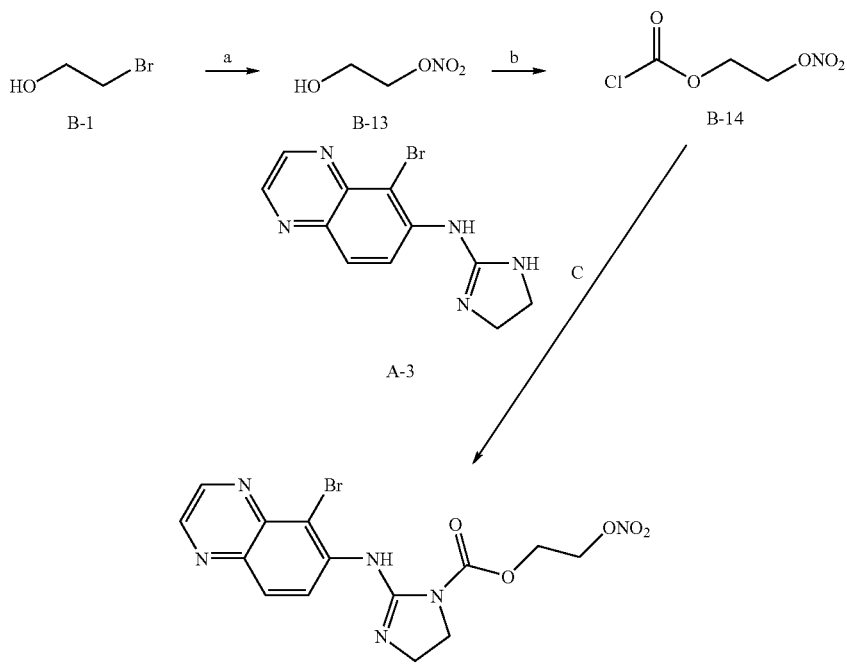

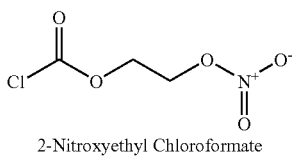

(B-14)

2-Nitroxyethyl Chloroformate

Compound B-13 (1.07 g, 10 mmol) was added to a cold solution of triphosgene (1.485 g, 5 mmol) in benzene (10 mL). The mixture was stirred at 0° C. for more than 20 min. A solution of Et₃N (1.01 g, 10 mmol) in benzene (5 mL) was added dropwise to the reaction mixture. The solution was warmed to room temperature and stirred overnight. The excess phosgene was removed by bubbling a stream of dry nitrogen through. The reaction mixture was evaporated and the residues was dissolved in Et₂O, and filtered to remove the salt. The collected solid was washed with Et₂O. The combined filtrate was evaporated under vacuum to give Compound B-14 as a light yellow oil (1.75 g) as light yellow oil. The crude product was used in the next step without further purification.

2-[5-Bromo-quinoxalin-6-ylimino]-imidazolidine-1-carboxylic Acid 2-nitrooxy-ethyl Ester To a solution of A-3 (120 mg, 0.411 mmol) in DMF (8.0 mL) was added Et N (166 mg, 1.643 mmol), followed by addition of the solution of B-14 (140 mg, 0.822 mmol) in Et₂O (0.5 mL) dropwise. The solution was stirred for 4 h at 65° C., and then for 40 h at room temperature. The mixture was evaporated under vacuum, and dissolved in CH₂Cl². The crude product was purified by preparative TLC (eluted with DCM/petroleum ether/EtOAc=2:2:0.5) to give compound B as a white solid (59 mg, 34% yield). To determine whether the acylation occurred on the ring, as opposed to the exocyclic nitrogen between the rings as reported in analogous compounds by Kosasayama, A.; et al *Chem. Pharm. Bull. Jpn.* 1979, 831-840: 2D ROSY ¹HNMR experiments showed interactions of the hydrogens on the ring and ethoxy as depicted below. Although this does not totally eliminate the possibility of the alternative regioisomer, molecular mechanics calculations indicate a higher energy conformation must be adopted to observe the interactions seen experimentally.

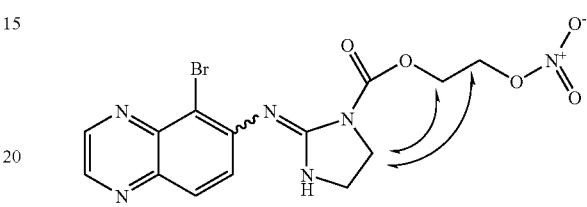

HPLC: 98.3% Purity. Column: Luna 5 µ C18 (2) ; Retention Time: 8.440 min; Mobile phase: methanol: 0.01% aqueous TFA=25:75, Wavelength: 254 nm.

$^1$H NMR (400 MHz, CDCl₃): δ 3.97 (m, 4H, =N—CH₂—CH₂—NCO), 4.60 (t, J=4.0 Hz, 2H, COOCH₂), 4.81 (t, J=4.0 Hz, 2H, CH₂ONO₂) , 8.09 (d, J=9.6 Hz, 1H, Ar—H), 8.77 (d, J=1.6 Hz, 1H, =N—CH=CH—N=), 8.91 (d, J=1.6 Hz, 1H, =N—CH=CH—N=), 9.28 (d, J=9.6 Hz, 1H, Ar—H), 10.35(s, 1H, —NH—).

MS (M+Na⁺): 447.2.

Scheme for Example 2

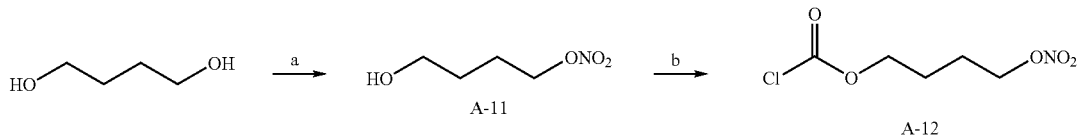

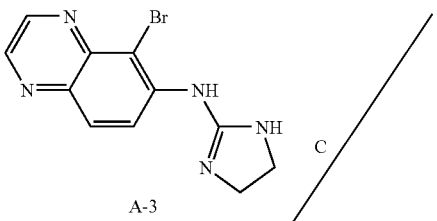

A-3 c

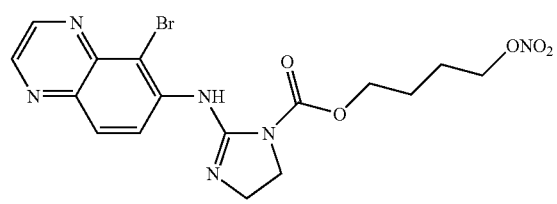

Reagents and conditions: a) ZnNO₃, DCC, CH₃CN, r.t.; b) Triphosgene, Et₃N, benzene, 0-20° C., 12 h; c) Et₃N, DMF, 64 h.

EXAMPLE 2

2-[5-Bromo-quinoxalin-6-ylimino]-imidazolidine-1-carboxylic Acid 4-Nitrooxy-butyl Ester

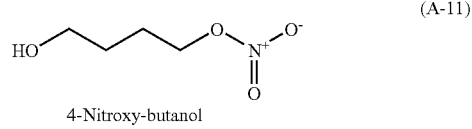

4-Nitroxy-butanol

According to a preparation from *Environ. Sci. Technol.* 2000, 34, 1197-1203, to a mixture of zinc nitrate hexahydrate (15 g) and acetonitrile (125 mL) was added 1,4-butanediol (20 mmol), followed by addition of N, N'-dicyclohexylcarbodiimide (10.3 g, 20 mmol). The reaction mixture was kept cold with ice-water bath, and then warmed and stirred at room temperature overnight. The white precipitate was filtered off, and the filtrate was evaporated under vacuum to give Compound A-11 as a yellow oil (8.5 g). The crude product was used in the next step without further purification, but matched the cited reported NMR data.

$^1$H NMR (400 MHz, CDCl): δ 1.69 (m, 2H, —CH₂—), 1.85 (m, 2H, —CH₂—), 3.69 (t, 2H, J=6.0 Hz, CH₂OH), 4.50 (t, 2H, J=6.0 Hz, CH₂ONO₂).

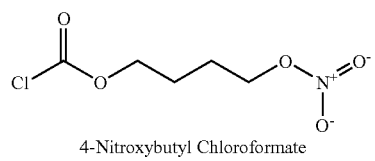

4-Nitroxybutyl Chloroformate

Alcohol A-11 (0.7 g) was added to a cold solution of triphosgene (0.77 g) in benzene (5 mL). The mixture was stirred at 0° C. for more than 20 min. The solution of Et₃N (0.53 g) in benzene (5 mL) was added dropwise to the reaction mixture. The mixture was warmed to room temperature and stirred overnight. The excess phosgene was removed by bubbling a stream of dry nitrogen through. Then the reaction mixture was evaporated and the residues was dissolved in Et₂O, and filtered to remove the salt. The collected solid was washed with Et₂). The combined filtrate was evaporated under vacuum to give Compound A-12 as a light yellow oil (0.5 g). The crude product was used in the next step without further purification.

2-[5-Bromo-quinoxalin-6-ylimino]-imidazolidine-1-carboxylic Acid 4-Nitrooxy-butyl Ester To a solution of A-3 (96 mg) in DMF (7.0 mL) was added Et₃N(133 mg), followed by a solution of A-12 (260 mg) in Et₂O (0.5 mL) dropwise. The solution was stirred for 4 h at 65° C., and at room temperature for 64 h. The solvent was evaporated under vacuum, and the residue was dissolved in CH₂C₂. The crude product was purified by preparative TLC (eluted with DCM/petroleum ether/EtOAc=2:2:0.5) to give compound A as a white solid (30 mg, 20% yield). The regiochemistry of this product was assumed by analogy to Example 1.

HPLC: 95.6% Purity. Column: Luna 5 μ C18 (2); Retention Time: 2.576 min.; Mobile phase: methanol: 0.01% aqueous TFA=48:52; Wavelength: 254 nm.

$^1$H NMR (400 MHz, CDCl): δ 1.90-1.93 (m, 4H, —CH₂—CH₂—), 3.90-3.99 (m, 4H, =N—CH₂—CH₂—NCO), 4.37 (s, 2H, COOCH₂), 4.56 (t, 2H, J=6.0 Hz, CH₂ONO₂), 8.09 (d, J=9.2 Hz, 1H, Ar—H), 8.78 (d, J=2.0 Hz, 1H, =N—CH=CH—N=), 8.92 (d, J=2.0 Hz, 1H, =N—CH=CH—N=), 9.31 (d, J=9.2 Hz, 1H, Ar—H), 10.49 (s, 1H, —NH—).

The invention claimed is:

1. A compound of formula (I) and pharmaceutically acceptable salts or stereoisomers thereof, $$A—X_1—Y—ONO_2 \quad (I)$$

wherein:

A is

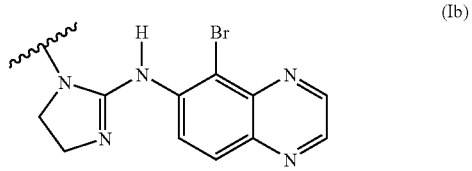

X₁ has the following meanings:
—C(O)—, —C(O)O—,

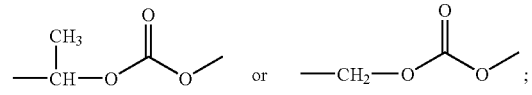

Y is selected from the group consisting of:
a) C₁ alkyl or straight or branched C₂-C₂₀ alkylene, being optionally substituted with one or more of the substituents selected from the group consisting of: halogen atoms, hydroxy, —ONO₂ and T₀,
wherein T₀ is
—OC(O)(C₁-C₁₀ alkyl)—ONO₂ or —O(C₁-C₁₀ alkyl)—ONO₂; or
cycloalkylene with 5 to 7 carbon atoms in the cycloalkylene ring, the ring being optionally substituted with side chains T, wherein T is an alkyl with 1 carbon atom or a straight or branched alkyl with from 2 to 10 carbon atoms;

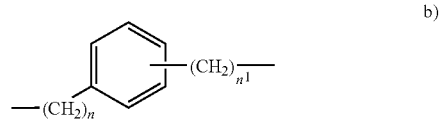

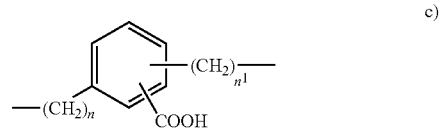

where n is an integer from 0 to 20,
n¹ is an integer from 1 to 20;

d)

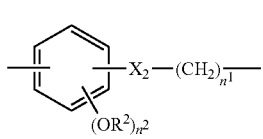

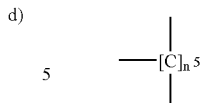

wherein n⁵ is as defined above;
Y² is selected from the group consisting of:

wherein:
$n^1$ is as defined above and $n^2$ is an integer from 0 to 2;
$X_2$=—OCO— or —COO— and $R^2$ is a hydrogen atom or $CH_3$;

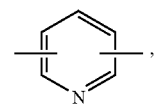 (Y1)

e)

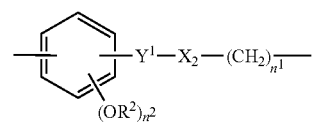

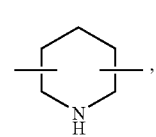 (Y2)

wherein:
$n^1$ and $n^2$, $R^2$, and $X_2$ are as defined above;
$Y^1$ is —CH$_2$—CH$_2$— or —CH=CH—(CH$_2$)n²—;

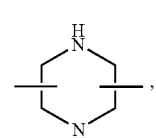 (Y3)

f)

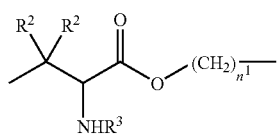

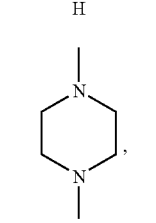 (Y4)

wherein:
$n^1$ and $R^2$ are as defined above, $R^3$ is H or —COCH$_3$;
with the proviso that when Y is one of b)-f), the —ONO$_2$ group is linked to a —(CH$_2$)$_{n1}$ group;

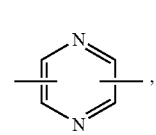 (Y5)

g)

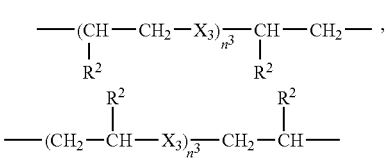

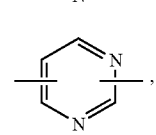 (Y6)

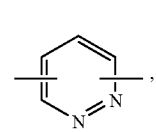 (Y7)

wherein $X_3$ is an oxygen atom or a sulphur atom,
$n^3$ is an integer from 1 to 6,
$R^2$ is as defined above; and

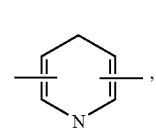 (Y8)

h)

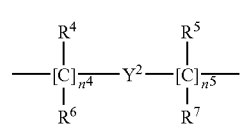

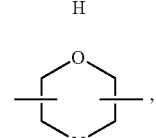 (Y9)

wherein:
$n^4$ is an integer from 0 to 10;
$n^5$ is an integer from 1 to 10;
$R^4, R^5, R^6, R^7$ are the same or different, and are H or a C$_1$ alkyl or straight or branched C$_2$-C$_4$ alkyl, wherein the —ONO$_2$ group is linked to

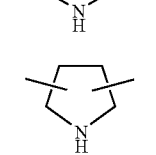 (Y10)

-continued (Y11)

(Y12), and (Y13).

2. The compound according to claim 1 wherein $X_1$ is —C(O)— or —C(O)O—,

Y is selected from the group consisting of:

a) a $C_1$ alkyl or straight or branched $C_2$-$C_{20}$ alkylene, b) —(CH$_2$)$_n$—[phenyl]—(CH$_2$)$_{n^1}$— c) —(CH$_2$)$_n$—[phenyl(COOH)]—(CH$_2$)$_{n^1}$— wherein n is an integer from 0 to 20, $n^1$ is an integer from 1 to 20; and g) —(CH(R$^2$)—CH$_2$—X$_3$)$_{n^3}$—CH(R$^2$)—CH$_2$—,
—(CH$_2$—CH(R$^2$)—X$_3$)$_{n^3}$—CH$_2$—CH(R$^2$)— wherein $X_3$ is an oxygen atom or a sulphur atom, $n^3$ is an integer from 1 to 6, $R^2$ is a hydrogen atom.

3. A compound selected from the group consisting of:

-continued
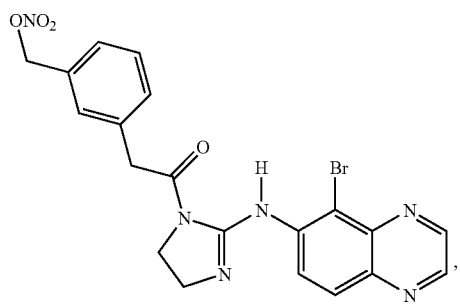
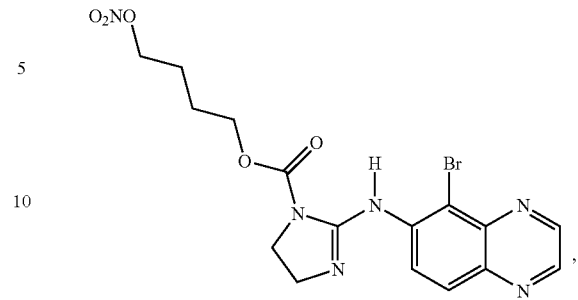
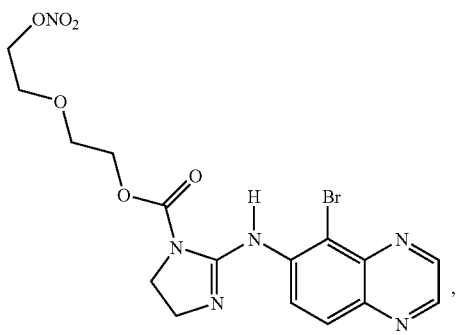
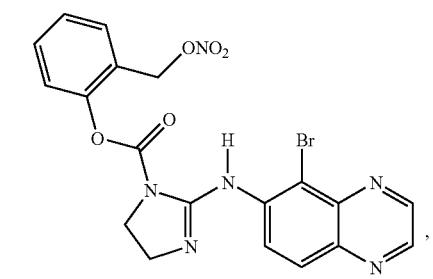
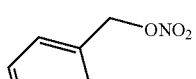
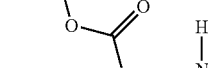
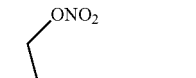
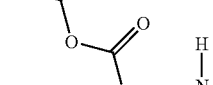

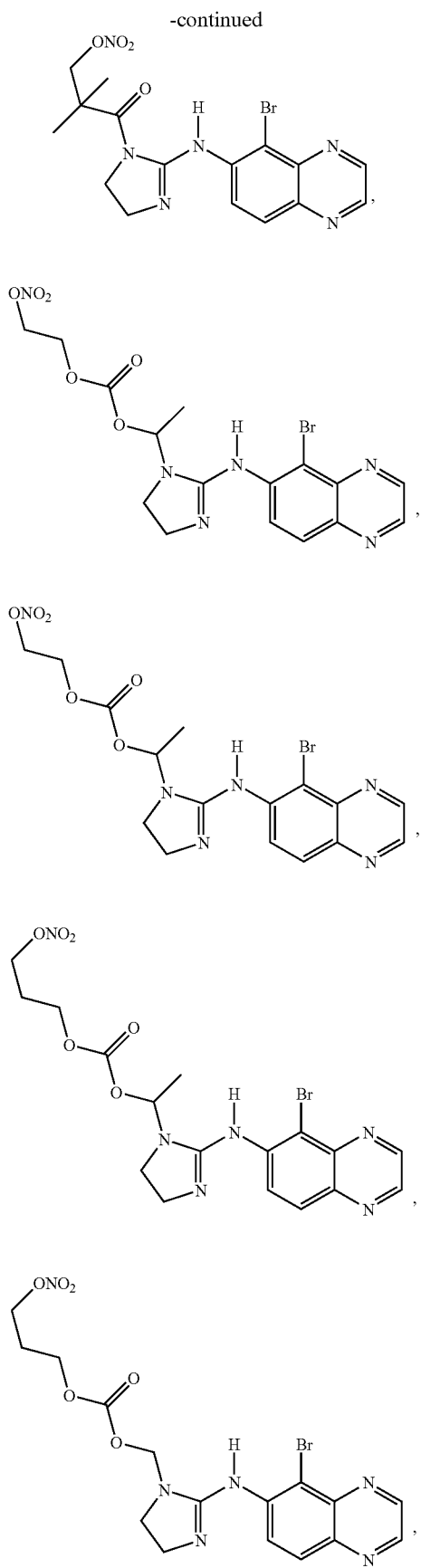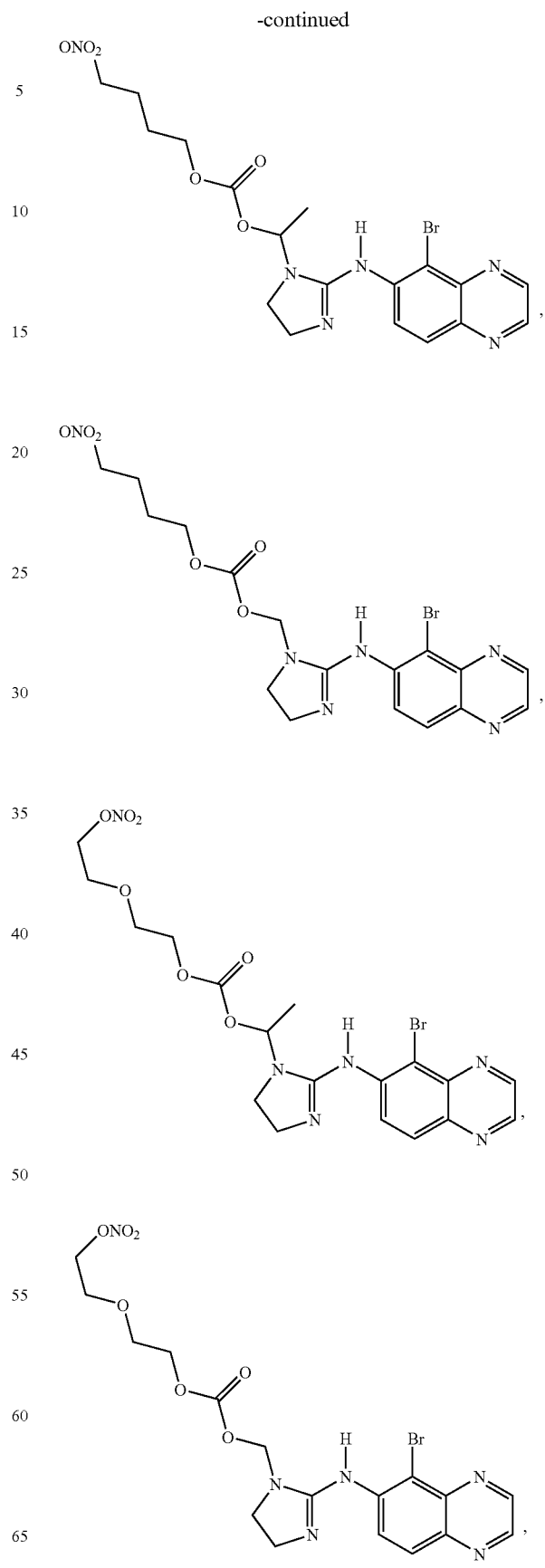

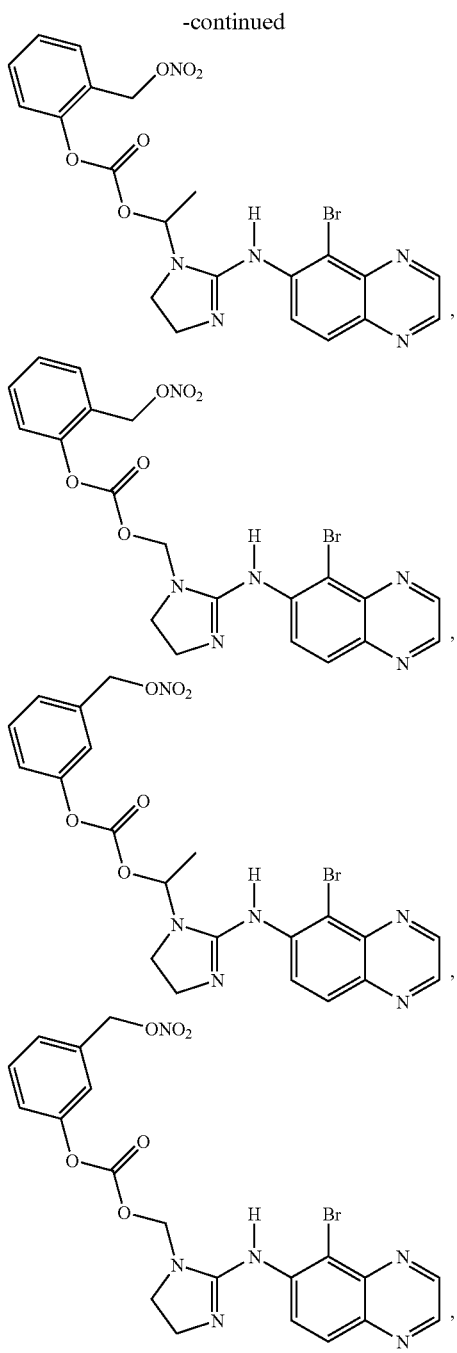

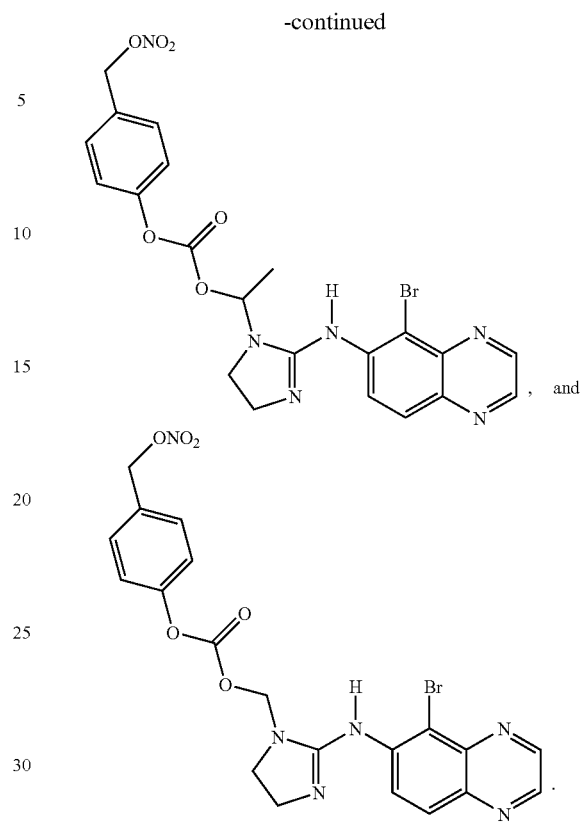

4. A pharmaceutical composition comprising a pharmaceutically acceptable carrier and a pharmaceutically effective amount of a compound according to claim 1.

5. A pharmaceutical composition comprising a pharmaceutically effective amount of a compound according to claim 1, wherein the pharmaceutical composition is in the form of a solution, suspension or emulsion, in an ophthalmically acceptable vehicle.

6. The compound according to claim 1, wherein Y is a $C_1$ alkyl or straight or branched $C_2$-$C_{10}$ alkylene, optionally substituted with one or more of the substituents selected from the group consisting of: halogen atoms, hydroxy, —$ONO_2$ and $T_0$, wherein $T_0$ is —$OC(O)(C_1$-$C_{10}$ alkyl)—$ONO_2$ or —$O(C_1$-$C_{10}$ alkyl)—$ONO_2$.

* * * * *